US00PP33921P2

(12) United States Plant Patent
Lannes

(10) Patent No.: US PP33,921 P2
(45) Date of Patent: Feb. 1, 2022

(54) ***MANDEVILLA* PLANT NAMED 'LANSOUTHDAKOTA'**

(50) Latin Name: *Mandevilla sanderi*
Varietal Denomination: Lansouthdakota

(71) Applicant: Robert Lannes, Malause (FR)

(72) Inventor: Robert Lannes, Malause (FR)

(73) Assignee: D.H.M. Innovation S.A.S., Malause (FR)

( * ) Notice: Subject to any disclaimer, the term of this patent is extended or adjusted under 35 U.S.C. 154(b) by 0 days.

(21) Appl. No.: 17/357,355

(22) Filed: Jun. 24, 2021

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 5/02
See application file for complete search history.

(56) References Cited

PUBLICATIONS https://www.floraldaily.com/article/9318265/innovation-is-the-action-to-bring-new-outstanding-varieties-to-the-market/; May 7, 2021; 4 pages.*

* cited by examiner

*Primary Examiner* — Kent L Bell
(74) *Attorney, Agent, or Firm* — C. Anne Whealy

(57) ABSTRACT

A new and distinct cultivar of *Mandevilla* plant named 'Lansouthdakota', characterized by its broadly upright and semi-vining plant habit; moderately vigorous growth habit; glossy dark green-colored leaves; early and freely flowering habit; and large flowers with pale yellow and yellowish pink-colored petals with reddish orange-colored star-shaped centers.

2 Drawing Sheets

Figure 1:
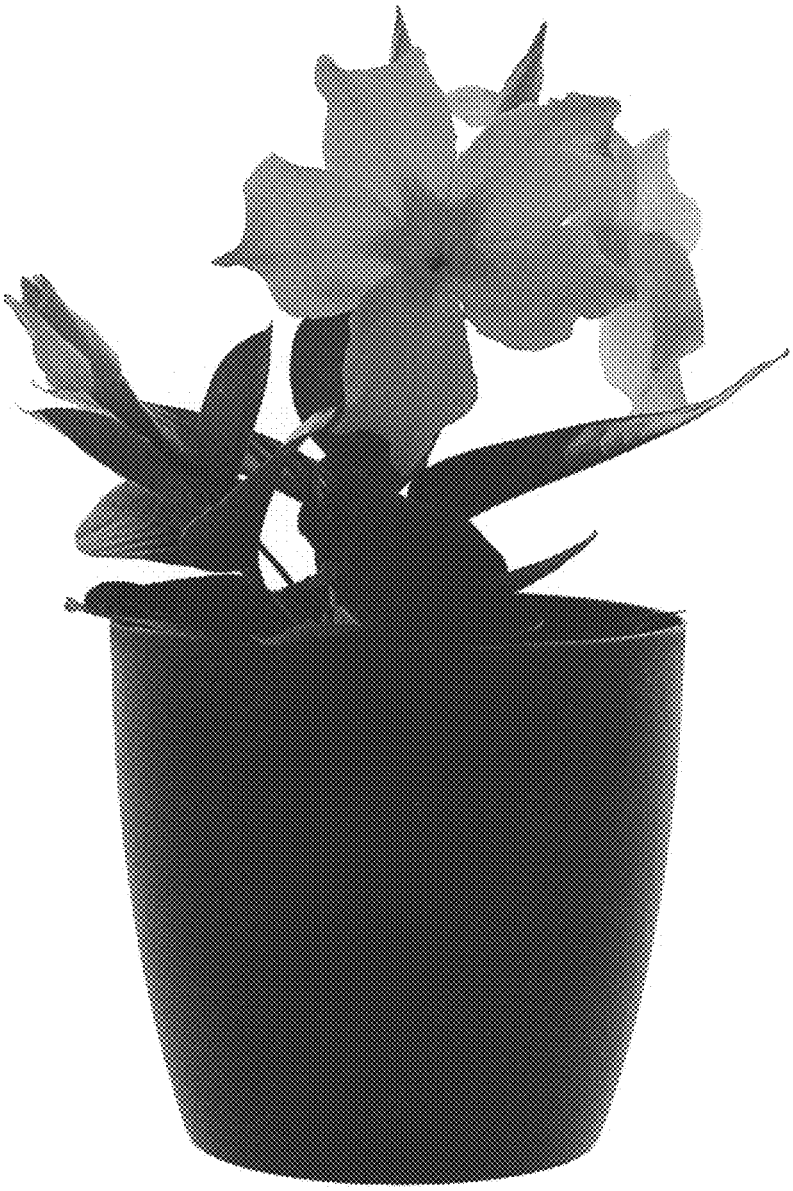

Botanical designation: *Mandevilla sanderi.*
Cultivar Denomination: 'LANSOUTHDAKOTA'.

STATEMENT REGARDING PRIOR DISCLOSURES BY THE INVENTOR/APPLICANT & ASSIGNEE

An European Community Plant Breeder's Rights application for the instant plant was filed by the D.H.M. Innovations S.A.S. of Malause, France on Nov. 30, 2020, application number 2020/3084. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Mandevilla* plant, botanically known as *Mandevilla sanderi* and hereinafter referred to by the name 'Lansouthdakota'.

The new *Mandevilla* plant is a product of a planned breeding program conducted by the Inventor in Malause, France. The objective of the breeding program is to create new freely branching *Mandevilla* plants with numerous unique and attractive flowers.

The new *Mandevilla* plant originated from a cross-pollination conducted by the Inventor in Malause, France in July, 2017 of a proprietary selection of *Mandevilla sanderi* identified as code number si 14-0028-002, not patented, as the female, or seed, parent with *Mandevilla sanderi* 'Sunpapri', disclosed in U.S. Plant Pat. No. 28,277, as the male, or pollen, parent. The new *Mandevilla* plant was discovered and selected by the Inventor as a single flowering plant from within the progeny of the stated cross-pollination in a controlled greenhouse environment in Malause, France in June, 2018.

Asexual reproduction of the new *Mandevilla* plant by stein cuttings in a controlled greenhouse environment in Malause, France since August, 2019 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Lansouthdakota'. These characteristics in combination distinguish 'Lansouthdakota' as a new and distinct *Mandevilla* plant:

1. Broadly upright and semi-vining plant habit.
2. Moderately vigorous growth habit.
3. Glossy dark green-colored leaves.
4. Early and freely flowering habit.
5. Large flowers with pale yellow and yellowish pink-colored petals with reddish orange-colored star-shaped centers.

Plants of the new *Mandevilla* can be compared to plants of the female parent selection. Plants of the new *Mandevilla* differ primarily from plants of the female parent selection in the following characteristics:

1. Plants of the new *Mandevilla* are more vigorous than plants of the female parent selection.
2. Leaves of plants of the new *Mandevilla* are narrower than and not as rounded as leaves of plants of the female parent selection.
3. Plants of the new *Mandevilla* have pale yellow and yellowish pink-colored petals with reddish orange-colored star-shaped centers whereas plants of the female parent selection have yellow-colored petals.

Plants of the new *Mandevilla* can be compared to plants of the male parent, 'Sunpapri'. Plants of the new *Mandevilla* differ primarily from plants of 'Sunpapri' in the following characteristics:

1. Plants of the new *Mandevilla* have sturdier flower petals than plants of 'Sunpapri'.
2. Plants of the new *Mandevilla* have pale yellow and yellowish pink-colored petals with reddish orange-colored star-shaped centers whereas plants of 'Sunpapri' have light to pale orange-colored petals.
3. Flowers of plants of the new *Mandevilla* resist color fading under full sunlight conditions whereas flowers of plants of 'Sunpapri' fade under full sunlight conditions.

Plants of the new *Mandevilla* can also be compared to plants of *Mandevilla sanderi* 'Lancalifornia', disclosed in U.S. Plant Pat. No. 24,074. In side-by-side comparisons, plants of the new *Mandevilla* differ primarily from plants 'Lancalifornia' in the following characteristics:

1. Plants of the new *Mandevilla* are more compact than plants of 'Lancalifornia'.
2. Leaves of plants of the new *Mandevilla* are narrower than and not as rounded as leaves of plants of 'Lancalifornia'.
3. Flowers of plants of the new *Mandevilla* are star-shaped whereas flowers of plants of 'Lancalifornia' are more rounded.
4. Plants of the new *Mandevilla* have pale yellow and yellowish pink-colored petals with reddish orange-colored star-shaped centers whereas plants of 'Lancalifornia' have yellow-colored petals.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) comprises a side perspective view of a typical flowering plant of 'Lancalifornia' grown in a container.

Figure 2:
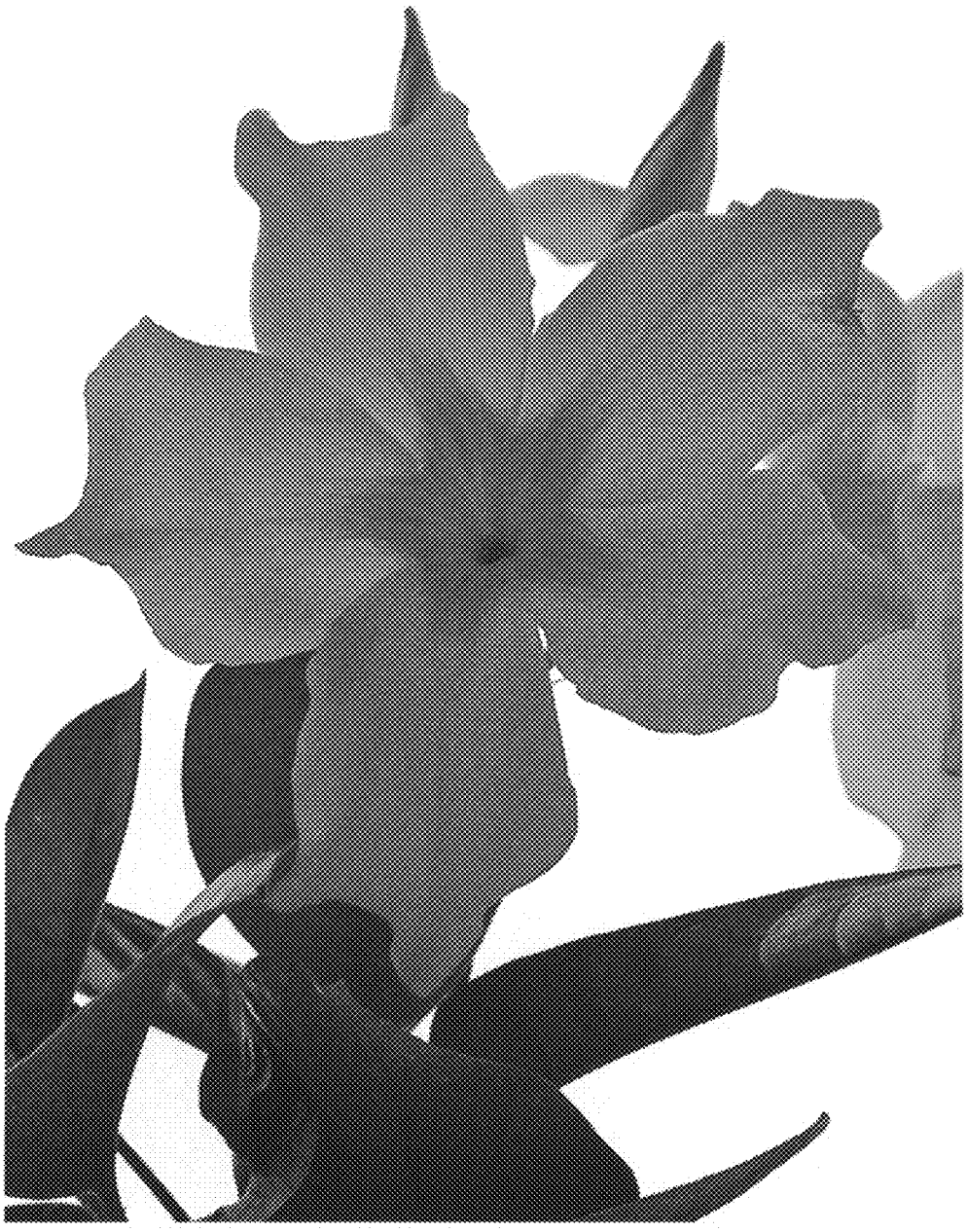

The photograph on the second sheet (FIG. 2) is a close-up view of a typical flower of 'Lancalifornia'.

DETAILED BOTANICAL DESCRIPTION

The aforementioned photographs and following observations, measurements and values describe plants grown during the autumn in 11-cm containers in a polyethylene-covered greenhouse in Malause, France and under cultural practices typical of commercial *Mandevilla* production. During the production of the plants, day temperatures ranged from 18° C. to 30° C. and night temperatures ranged from 15° C. to 18° C. Plants were ten months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'Lansouthdakota'.

Parentage:

*Female, or seed, parent.*—Proprietary selection of *Mandevilla sanderi* identified as code number si 14-0028-002, not patented.

*Male, or pollen, parent.*—*Mandevilla sanderi* 'Sunpapri', disclosed in U.S. Plant Pat. No. 28,277.

Propagation:

*Type.*—By vegetative stein cuttings.

*Time to initiate roots, summer.*—About two weeks at temperatures about 23° C. to 30° C.

*Time to initiate roots, winter.*—About three weeks at temperatures about 18° C. to 21° C.

*Time to produce a rooted young plant, summer.*—About five to six weeks at temperatures about 23° C. to 30° C.

*Time to produce a rooted young plant, winter.*—About six to eight weeks at temperatures about 18° C. to 21° C.

*Root description.*—Fine, fibrous; typically light yellowish white in color, actual color of the roots is dependent on substrate composition, water quality, fertilizers, substrate temperature and physiological age of roots.

*Rooting habit.*—Freely branching; medium density.

Plant description:

*Plant and growth habit.*—Broadly upright and semi-vining plant habit; overall plant shape, broadly oblong to obovate; moderately vigorous growth habit and moderate to slow growth rate.

*Plant height, soil level to top of foliar plane.*—About 15.1 cm.

*Plant height, soil level to top of floral plane.*—About 16 cm.

*Plant diameter (spread).*—About 17.6 cm.

*Lateral branch description.*—Branching habit: Typically two primary lateral branches each with about one or two secondary lateral branches developing per plant. Length: About 8.3 cm. Diameter: About 2.5 mm. Internode length: About 2.6 cm. Aspect: Primary lateral branches, mostly erect; secondary lateral branches, about 25° to 45° from primary branch axis. Strength: Strong. Texture and luster: Smooth, glabrous; moderately glossy; becoming woody with development. Color, developing: Close to 145A.

*Color, developed.*—Close to between 143C and 144B; when woody, close to 199A.

Leaf description:

*Arrangement*.—Opposite, simple.

*Length*.—About 8.9 cm.

*Width*.—About 5 cm.

*Shape*.—Broadly ovate to broadly elliptic and broadly oblong.

*Apex*.—Apiculate.

*Base*.—Truncate.

*Margin*.—Entire; slightly undulate.

*Texture and luster, upper surface*.—Smooth, glabrous; moderately coriaceous; glossy.

*Texture and luster, lower surface*.—Smooth, glabrous; moderately coriaceous; moderately glossy.

*Venation pattern*.—Pinnate.

*Color*.—Developing leaves, upper surface: Close to 144A. Developing leaves, lower surface: Close to 144B. Full expanded leaves, upper surface: Slightly darker and more intense than between 137A and 147A; venation, close to 144A. Fully expanded leaves, lower surface: Close to between 144A and 146B; venation, close to 146D.

*Petioles*.—Length: About 6 mm. Diameter: About 2.5 mm by 2.5 mm. Strength: Moderately strong. Texture and luster, upper surface: Smooth, glabrous; moderately glossy. Texture and luster, lower surface: Smooth, glabrous; slightly glossy. Color, upper surface: Close to 144A. Color, lower surface: Close to 144B.

Flower description:

*Flower type and flowering habit*.—Single salverform flowers arranged singly or in terminal or axillary cymes; flowers star-shaped and face mostly outwardly to slightly upright; freely flowering habit with about six flower buds and flowers developing per plant.

*Natural flowering season*.—Plants flower continuously from spring into the autumn in France; early flowering habit, plants in full flower about six to seven months after planting.

*Flower longevity on the plant*.—About ten days; flowers not persistent.

*Fragrance*.—None detected.

*Inflorescence height*.—About 7.6 cm.

*Inflorescence diameter*.—About 11.5 cm.

*Flower buds*.—Length: About 6.2 cm. Diameter: About 1.2 cm. Shape: Narrowly oblanceolate. Texture and luster: Smooth, glabrous; slightly glossy. Color: Distally, close to 16C and 16D and proximally, close to 154B; tube, close to 144C.

*Flowers*.—Appearance: Flared trumpet, corolla fused and five-parted. Diameter: Large, about 10 cm. Depth (length): About 4.5 cm. Throat diameter: About 9 mm. Tube length: About 3.6 cm. Tube diameter: Distally, about 1.2 cm; proximally, about 3.5 mm.

*Petals*.—Quantity and arrangement: Five petals arranged in a single whorl; lower 42% portion of the petals are fused into a funnelform tube. Petal length: About 8.6 cm. Petal width: About 4.5 cm. Petal shape: Unequal spatulate; moderately convex. Petal apex: Apiculate. Petal margin: Entire; moderately undulate. Petal texture and luster, upper surface: Smooth, glabrous; not rugose; velvety; matte to slightly glossy. Petal texture and luster, lower surface: Smooth, glabrous; not rugose; slightly velvety; matte. Throat texture: Smooth, glabrous; velvety. Tube texture: Smooth, glabrous; slightly velvety. Color: Petal, when opening, upper surface: Close to 16C; towards the margins, close to 24D; towards the apex, close to 31C to 31D. Petal, when opening, lower surface: Close to between 11B and 15D; towards the margins and apex, close to 25D. Petal, fully opened, upper surface: Close to 19C; towards the margins, close to 33D; towards the apex, close to 39B; towards the throat, star flushed with close to 32A and 32B; venation, similar to lamina; color does not change with subsequent development. Petal, fully opened, lower surface: Close to 18C; towards the margins and apex, close to 29C; venation, similar to lamina color; color does not change with subsequent development. Throat: Distally, close to 13A and proximally, close to N144A; venation, similar to lamina colors. Tube: Distally, close to 18C and proximally, close to 6C; towards the base, close to N144B; venation, similar to lamina colors.

*Sepals*.—Quantity and arrangement: Five sepals arranged in a single whorl. Calyx length: About 1.4 cm. Calyx diameter: About 1.1 cm. Sepal length: About 1.4 cm. Sepal width: About 3 mm. Sepal shape: Lanceolate. Sepal apex: Narrowly acuminate. Sepal base: Broadly cuneate and fused at the base. Sepal margin: Entire. Sepal texture and luster, upper surface: Smooth, glabrous; slightly glossy. Sepal texture and luster, lower surface: Smooth, glabrous; matte. Sepal color: When opening, upper surface: Close to 145B. When opening, lower surface: Close to 145A. Fully opened, upper and lower surfaces: Close to 145B; at the apex, close to 180C.

*Peduncles*.—Length: About 5.5 cm. Diameter: About 2.25 mm. Strength: Strong. Aspect: About 20° from lateral branch axis. Texture and luster: Smooth, glabrous; slightly glossy. Color: Close to 145A.

*Pedicels*.—Length: About 1.1 cm. Diameter: About 2 mm. Strength: Strong. Aspect: About 20° from peduncle axis. Texture and luster: Smooth, glabrous; slightly glossy. Color: Close to 145A to 145B.

*Reproductive organs*.—Stamens: Quantity and arrangement: Typically five; basifixed; anthers connivent. Filament length: About 2 mm. Filament color: Close to 151D. Anther size: About 1.25 mm by 8 mm. Anther shape: Narrowly oblong. Anther color: Close to 161B. Pollen amount: None observed. Pistils: Quantity: Typically one. Pistil length: About 2 cm. Style length: About 1.7 cm. Style color: Close to 150C to 150D. Stigma diameter: About 2 mm. Stigma shape: Club-shaped, pointed. Stigma color: Close to 146D. Ovary color: Close to 144A.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures of about 5° C. to 40° C. and to be suitable for USDA Hardiness Zones 9 through 13.

It is claimed:

1. A new and distinct *Mandevilla* plant named 'Lansouth-dakota' as illustrated and described.

* * * * *